(12) United States Patent
Stanley et al.

(10) Patent No.: US 9,724,082 B2
(45) Date of Patent: Aug. 8, 2017

(54) DELIVERY SYSTEM FOR TISSUE OPENING CLOSURES

(71) Applicant: Cook Medical Technologies LLC, Bloomington, IN (US)

(72) Inventors: Cleon Stanley, Bloomington, IN (US); Tyler J. Bunch, Bloomington, IN (US); Jonathan Lee Bennett, Bloomington, IN (US); Ram H. Paul, Jr., Bloomington, IN (US); Brian L. Bates, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 172 days.

(21) Appl. No.: 14/211,513

(22) Filed: Mar. 14, 2014

(65) Prior Publication Data

US 2014/0277116 A1    Sep. 18, 2014

Related U.S. Application Data

(60) Provisional application No. 61/788,533, filed on Mar. 15, 2013.

(51) Int. Cl.
*A61B 17/00* (2006.01)
*A61B 17/04* (2006.01)
*A61B 90/00* (2016.01)

(52) U.S. Cl.
CPC ...... *A61B 17/0057* (2013.01); *A61B 17/0483* (2013.01); *A61B 2017/0061* (2013.01);
(Continued)

(58) Field of Classification Search
CPC ............ A61B 17/0057; A61B 17/0483; A61B 17/0401; A61B 2017/00623; A61B 2017/0061; A61B 2017/00575; A61B 2017/0496; A61B 2017/00637; A61B 2017/00615; A61B 2017/00659;
(Continued)

(56) References Cited

U.S. PATENT DOCUMENTS

| 4,744,364 A | 5/1988 | Kensey |
| 5,269,809 A | 12/1993 | Hayhurst et al. |

(Continued)

FOREIGN PATENT DOCUMENTS

| EP | 0 534 696 A1 | 3/1993 |
| EP | 0534696 A1 | 3/1993 |

(Continued)

OTHER PUBLICATIONS

International Search Report and Written Opinion issued in PCT/US2012/066173, dated Mar. 8, 2013.
(Continued)

*Primary Examiner* — Jocelin Tanner
(74) *Attorney, Agent, or Firm* — Woodard, Emhardt, Moriarty, McNett & Henry LLP

(57) ABSTRACT

Among other things, methods and apparatus for inserting devices for closing tissue openings are disclosed. Examples may include a handle, sheath and/or sleeve for insertion into a patient and through or adjacent a tissue defect, fistula, or other tissue opening to be closed. Winding mechanisms for operation in or with such inserting devices are also described.

14 Claims, 4 Drawing Sheets

(52) U.S. Cl.
CPC ........... *A61B 2017/00575* (2013.01); *A61B 2017/00623* (2013.01); *A61B 2017/0496* (2013.01); *A61B 2090/037* (2016.02)

(58) Field of Classification Search
CPC .. A61B 2017/00663; A61B 2017/0498; A61B 2017/00654; A61B 2017/0065
See application file for complete search history.

(56) References Cited

U.S. PATENT DOCUMENTS

| | | | |
|---|---|---|---|
| 5,312,435 A | 5/1994 | Nash et al. | |
| 5,342,393 A | 8/1994 | Stack | |
| 5,350,399 A | 9/1994 | Erlebacher et al. | |
| 5,411,520 A | 5/1995 | Nash et al. | |
| 5,531,759 A | 7/1996 | Kensey et al. | |
| 5,545,178 A | 8/1996 | Kensey et al. | |
| 5,620,461 A | 4/1997 | Muijs Van De Moer et al. | |
| 5,662,681 A | 9/1997 | Nash et al. | |
| 5,700,277 A | 12/1997 | Nash et al. | |
| 5,800,436 A | 9/1998 | Lerch | |
| 5,916,236 A | 6/1999 | Muijs Van de Moer | |
| 6,071,301 A | 6/2000 | Cragg et al. | |
| 6,190,400 B1 | 2/2001 | Van De Moer et al. | |
| 6,425,911 B1 | 7/2002 | Akerfeldt | |
| 6,491,714 B1 | 12/2002 | Bennett | |
| 6,508,828 B1 | 1/2003 | Akerfeldt et al. | |
| 6,596,013 B2 | 7/2003 | Yang et al. | |
| 6,755,868 B2 | 6/2004 | Rousseau | |
| 6,764,500 B1 | 7/2004 | Muijs Van De Moer et al. | |
| 6,860,895 B1 | 3/2005 | Akerfeldt et al. | |
| 6,921,401 B2 | 7/2005 | Lerch et al. | |
| 6,939,363 B2 | 9/2005 | Akerfeldt | |
| 7,048,710 B1 | 5/2006 | Cragg et al. | |
| 7,169,168 B2 | 1/2007 | Muijs Van De Moer et al. | |
| 7,338,514 B2 | 3/2008 | Wahr et al. | |
| 7,597,705 B2 | 10/2009 | Forsberg et al. | |
| 7,621,937 B2 | 11/2009 | Pipenhagen et al. | |
| 7,658,748 B2 | 2/2010 | Marino et al. | |
| 7,717,929 B2 | 5/2010 | Fallman | |
| 7,875,052 B2 | 1/2011 | Kawaura et al. | |
| 7,931,671 B2 | 4/2011 | Tenerz | |
| 7,993,367 B2 | 8/2011 | Bagaoisan et al. | |
| 8,105,352 B2 | 1/2012 | Egnelov | |
| 8,257,389 B2 | 9/2012 | Chanduszko et al. | |
| 8,480,709 B2 | 7/2013 | Chanduszko et al. | |
| 8,652,166 B2 | 2/2014 | Akerfeldt | |
| 2003/0181988 A1 | 9/2003 | Rousseau | |
| 2005/0085855 A1 | 4/2005 | Forsberg | |
| 2005/0169974 A1 | 8/2005 | Tenerz | |
| 2005/0283187 A1 | 12/2005 | Longson | |
| 2006/0135991 A1* | 6/2006 | Kawaura | A61B 17/0057 606/213 |
| 2006/0142797 A1 | 6/2006 | Egnelov | |
| 2006/0206146 A1 | 9/2006 | Tenerz | |
| 2006/0241579 A1* | 10/2006 | Kawaura | A61B 17/0057 606/39 |
| 2007/0123936 A1 | 5/2007 | Goldin et al. | |
| 2007/0198059 A1 | 8/2007 | Patel et al. | |
| 2008/0071310 A1 | 3/2008 | Hoffman et al. | |
| 2008/0114395 A1 | 5/2008 | Mathisen et al. | |
| 2008/0287986 A1 | 11/2008 | Thor et al. | |
| 2008/0312684 A1 | 12/2008 | Drasler et al. | |
| 2009/0018574 A1 | 1/2009 | Martin | |
| 2009/0054926 A1 | 2/2009 | Pipenhagen et al. | |
| 2009/0088793 A1 | 4/2009 | Bagaoisan et al. | |
| 2009/0112257 A1 | 4/2009 | Preinitz | |
| 2009/0143817 A1 | 6/2009 | Akerfeldt | |
| 2009/0216267 A1 | 8/2009 | Willard et al. | |
| 2009/0234377 A1 | 9/2009 | Mahlin | |
| 2010/0042144 A1 | 2/2010 | Bennett | |
| 2010/0087854 A1 | 4/2010 | Stopek et al. | |
| 2010/0217308 A1 | 8/2010 | Hansen et al. | |
| 2010/0217309 A1 | 8/2010 | Hansen et al. | |
| 2011/0066181 A1 | 3/2011 | Jenson et al. | |
| 2011/0178537 A1* | 7/2011 | Whitman | A61B 17/0057 606/144 |
| 2011/0288581 A1 | 11/2011 | Paul et al. | |
| 2012/0116447 A1 | 5/2012 | Stanley et al. | |
| 2012/0277791 A1* | 11/2012 | Abo-Auda | A61B 17/0057 606/213 |

FOREIGN PATENT DOCUMENTS

| | | |
|---|---|---|
| EP | 1 169 968 A1 | 1/2002 |
| EP | 1 169 968 A1 | 1/2002 |
| EP | 1 266 626 A1 | 12/2002 |
| EP | 1 413 255 A1 | 4/2004 |
| EP | 1 440 661 | 7/2004 |
| EP | 2 064 999 A2 | 6/2009 |
| EP | 2064999 A2 | 6/2009 |
| WO | WO 99/33402 | 7/1999 |
| WO | WO 00/078226 | 12/2000 |
| WO | WO 2005/063133 A1 | 7/2005 |
| WO | WO 2006/075228 | 7/2006 |
| WO | WO 2007/059243 A1 | 5/2007 |
| WO | WO 2011/146729 A2 | 11/2011 |

OTHER PUBLICATIONS

International Search Report and Written Opinion issued in PCT/US2011/037173, dated Nov. 17, 2011.

* cited by examiner

DELIVERY SYSTEM FOR TISSUE OPENING CLOSURES

This application claims the benefit of U.S. Provisional Application Ser. No. 61/788,533, filed on Mar. 15, 2013, which is incorporated herein by reference in its entirety.

This disclosure relates to medical devices for closing tissue openings. In particular, this disclosure describes devices within which closures (e.g. closures for patent foramen ovale or other septal defects) are at least partially placed, and which are used to insert and place such closures.

BACKGROUND

Many different types of devices for inserting a number of different types of closures into a hole or opening of a vessel or organ have been proposed. However, prior devices have been relatively large, requiring opening cannulae or other devices in order to be inserted to the site for treatment. There is a need for smaller, more maneuverable and flexible devices for placing closure devices.

SUMMARY

Among other things, there are disclosed embodiments of apparatus and methods for inserting or otherwise applying a closure to a bodily opening, such as patent foramen ovale, a fistula, a hole in a vessel wall made for access to the vessel (e.g. a blood vessel), or other defects or injuries. For example, an apparatus for inserting a device into a patient to close a tissue opening in the patient can include a handle portion having a gripping portion with an external surface for gripping by a user, a lumen extending through the gripping portion and a cap. A sleeve having a proximal end and a flange at the proximal end, the sleeve defining a lumen, and a sheath portion having a proximal end portion with a cap for selectively connecting with the cap or the handle portion and an elongated tubular member extending from the proximal end portion, with a lumen extending through the proximal end portion and the elongated tubular member, may also be provided. The elongated tubular portion of the handle portion extends at least partially through the lumen of the sheath portion, and the elongated tubular member of the sheath portion extends at least partially through the lumen of the sleeve, and wherein the sleeve and tubular member of the sheath portion are slidable with respect to each other along each other. A closure device having an internal anchor member and a filament connected to the internal anchor member is provided in particular embodiments, with the internal anchor member being initially within the sheath portion and the filament initially extending through at least a portion of the lumen of the sheath portion and the lumen of the handle portion.

Embodiments of the apparatus may include a winding mechanism connected to the handle portion, the winding mechanism having a knob operatively connected to the filament so that when the knob is turned in a predetermined direction, tension is applied to the filament. Examples of such winding mechanisms include an axle to which the filament is connected, wherein turning the knob turns the axle and winds the filament. Other examples of winding mechanisms may press or move the handle portion proximally with respect to sheath and/or sleeve, so as to apply tension to the filament.

Apparatus embodiments can include or be associated with a hemostatic valve, particularly in cases where the opening to be closed is accessible via the circulatory system or is in a blood vessel. For example, the apparatus can include a hemostatic valve for percutaneous insertion in a blood vessel, and wherein at least a portion of the sleeve extends through the valve to allow at least a portion of the sheath and the sealing member into the vessel, for maneuvering to a closure site such as within the heart. The sleeve portion may be configured for insertion through a hemostatic valve, with a flange of the sleeve configured to engage the valve, so that the flange cannot move entirely through the valve. Seals may also be placed within the handle. For example, the handle portion may include an internal seal adapted for allowing the filament to pass through in sealing engagement.

Methods are also disclosed herein, include embodiments of inserting a closure device into a patient for closing an undesirable tissue opening. Such methods can include inserting an apparatus into the patient, wherein the apparatus includes a handle portion with a gripping portion, a distal cap, and a lumen extending through the gripping portion and cap, a sleeve defining a lumen and having a proximal end and a flange at the proximal end, and a sheath portion having a proximal end portion with a cap for selectively connecting to and separating from the cap on the handle and an elongated tubular member extending from the proximal end portion with a lumen extending through the proximal end portion and the elongated tubular member. The elongated tubular member of the sheath portion extends at least partially through the lumen of the sleeve, and the sleeve and tubular member of the sheath portion are slidable with respect to each other along each other. The handle portion can be pulled so that it moves proximally with respect to the sleeve, so as to engage an anchoring member with tissue adjacent the undesirable tissue opening, the anchoring member being connected to a filament that extends proximally through the handle portion. The connection between the filament and the anchoring member is severed.

In particular examples of such methods, e.g. where the tissue opening to be closed is a hole in a cardiac septum, the insertion of the device into the patient includes inserting through a hemostatic valve accessing the vessel. Examples are provided in which the apparatus includes a winding mechanism operatively connected to the filament, and wherein the severing step includes operating the winding mechanism to apply tension to the filament. For instance, the severing step may include operating the winding mechanism at least until the filament breaks, and/or operating the winding mechanism at least until a proximal portion of the anchoring member breaks.

Figure 1:
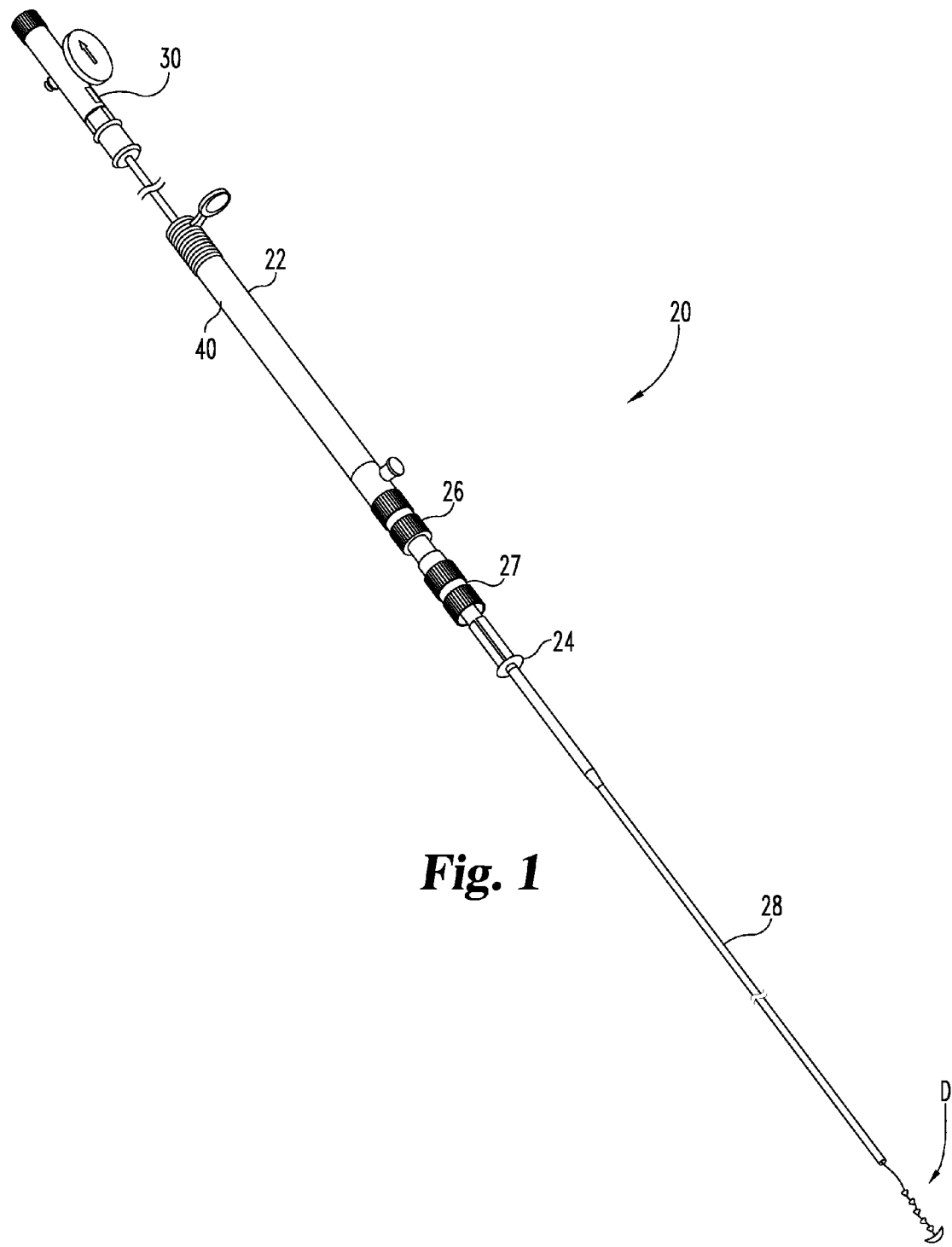
FIG. 1 is a perspective view of an embodiment of a closure application device as disclosed herein.
Figure 2A:
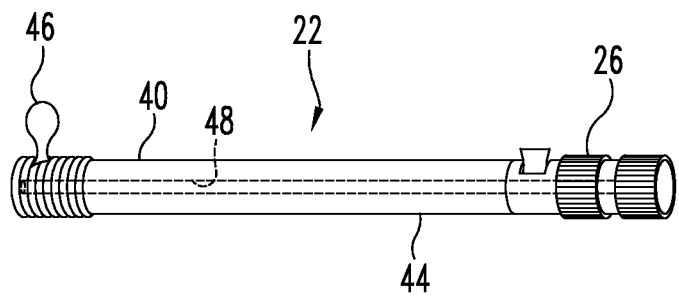
FIG. 2A is a side perspective view of a portion of the embodiment shown in FIG. 1.
Figure 2B:
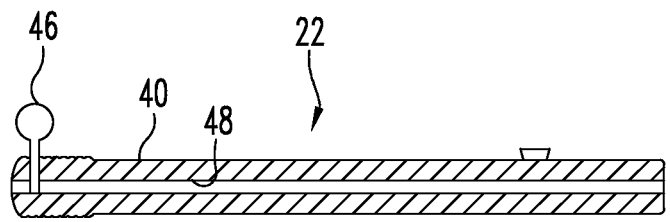
FIG. 2B is a part cross-sectional view of the portion shown in FIG. 2A.
Figure 3A:
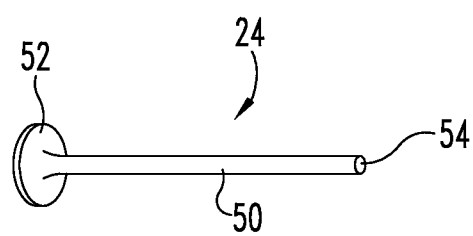
FIG. 3A is a side perspective view of a portion of the embodiment shown in FIG. 1.
Figure 3B:
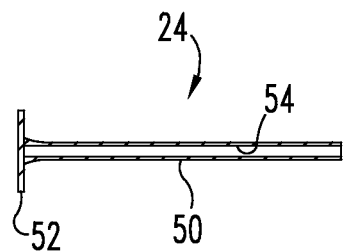
FIG. 3B is a part cross-sectional view of the portion shown in FIG. 3A.
Figure 4A:
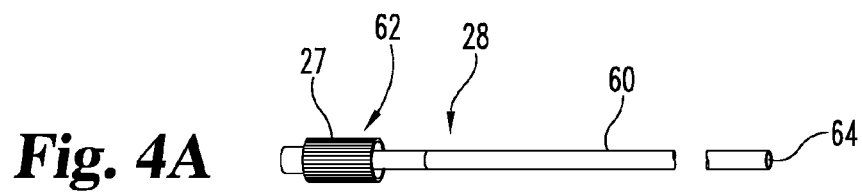
FIG. 4A is a side perspective view of a portion of the embodiment shown in FIG. 1.
Figure 4B:
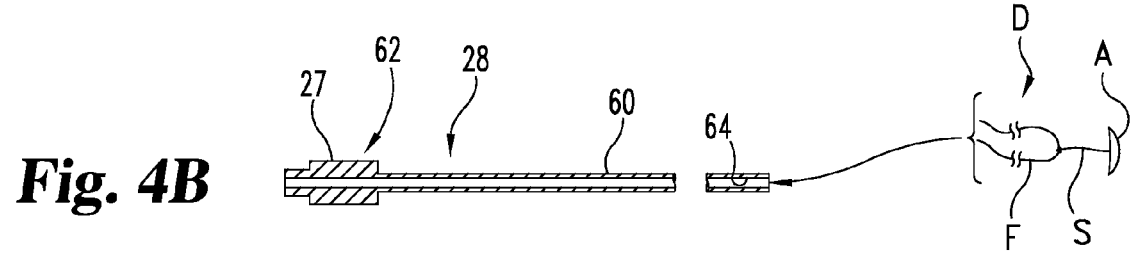
FIG. 4B is a part cross-sectional view of the portion shown in FIG. 4A.
Figure 5A:
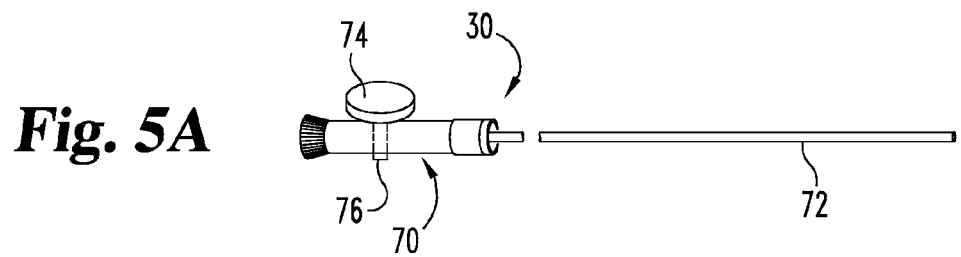
FIG. 5A is a side perspective view of a portion of the embodiment shown in FIG. 1.
Figure 5B:
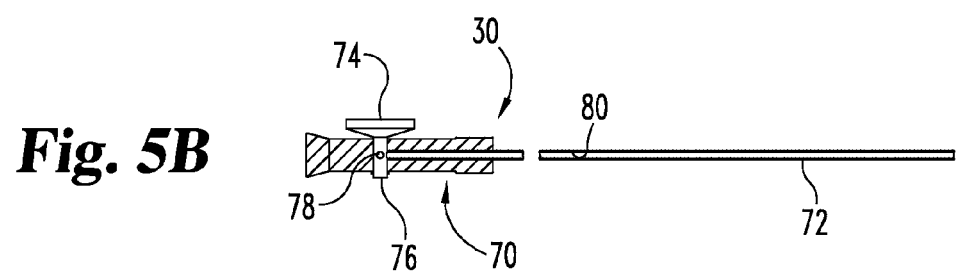
FIG. 5B is a part cross-sectional view of the portion shown in FIG. 5A.

DETAILED DESCRIPTION OF THE
ILLUSTRATED EMBODIMENTS

To promote an understanding of the principles of the disclosure, reference will now be made to certain embodiments and specific language will be used to describe the same. It will nevertheless be understood that no limitation of the scope of the claims is thereby intended, such alterations and further modifications of the disclosed methods and/or devices, and such further applications of the principles of the disclosure as described herein, being contemplated as would normally occur to one skilled in the art to which the disclosure relates.

Referring now generally to the figures, there is shown an embodiment of a delivery system 20 for inserting and applying devices for closing holes in tissue, such as septal defects (e.g. patent foramen ovale, or PFO), fistulae, or holes formed in tissue during diagnosis or treatment. Devices D insertable by system 20 are described in brief terms below, and it will be understood that examples of such devices are disclosed in application Ser. No. 13/111,338 (filed on May 19, 2011), Ser. No. 13/303,707 (filed on Nov. 23, 2011), Ser. No. 61/716,182 (filed on Oct. 19, 2012) and Ser. No. 61/716,155 (filed on Oct. 19, 2012), all of which are incorporated herein by reference in their entireties.

System 20, in the illustrated embodiment, includes a delivery handle 22, an introducer sleeve 24, tips or caps 26, 27 that can abut or link handle 22 and an extending sheath 28. As will be discussed further below, handle 22 is held by the user during insertion and use of system 20. A winding mechanism 30 is provided in particular embodiments, to provide increasing tension on a suture extending through handle 22, sleeve 24, and sheath 28 and into the patient.

Handle 22 has a generally cylindrical holding portion 40, and tip or cap 26 is fixed to the distal end of holding portion 40, for facing or linking to tip or cap 27 of sheath 28 as noted. An outer surface 44 of holding portion 40 is sized and configured (e.g. with texturing or high-friction material, in particular embodiments) for comfortable holding in a user's hand. A proximal lock 46 is provided in the illustrated embodiment, extending through outer surface 44 of holding portion 40 and into lumen 48. In a particular embodiment, lock 46 has a circular, curved or otherwise enlarged grip and a projection through surface 44 and into lumen 48. The projection is configured to provide a tight or interference fit between handle 22 and a portion of winding mechanism 30, so that when engaged lock 46 limits or prevents movement of winding mechanism 30 with respect to handle 22. Accordingly, the projection of lock 46 may be tapered to wedge into a hole through surface 44 and/or have a concave distal end to engage winding mechanism 30. Lumen 48 extends through holding portion 40 and cap 26.

Sleeve 24 includes a tube portion 50 extending distally from a flange or boss 52. A lumen 54 runs through the entirety of tube portion 50 and exits through flange 52. Sleeve 24 in a particular embodiment is of a thin plastic, with lumen 54 of a size sufficient to pass sheath 28 through. For example, lumen 54 can have a diameter just slightly larger than an outer diameter of sheath 28, so that sleeve 24 and sheath 28 have a relatively close fit (e.g. without substantial play between them) yet can move with respect to each other without substantial friction. It will be understood that materials can be chosen for one or both of sleeve 24 and sheath 28 to minimize friction between them.

The outer diameter of tube portion 50 is sized to fit through a hemostatic valve (e.g. FIG. 6) so that the valve seals around the exterior of tube portion 50. In that way, little or no fluid can escape from between tube portion 50 and the valve, and no air or other gases can enter through the valve. The illustrated embodiment of tube portion 50 has a uniform cylindrical exterior, although it will be understood that other exterior configurations may be provided. Flange 52 is substantially circular or disk-shaped in the illustrated embodiment, with a diameter that is substantially larger than an opening through the valve, so that flange 52 prevents sleeve 24 from moving fully through the valve. Flange 52 can also provide a sealing engagement within or against the top or other portion of the check flow valve. As will be discussed further below in an example, flange 52 may rest on the valve when system 20 is being inserted for use.

Sheath 28 has an elongated tube portion 60 extending distally from a head portion 62, which in this embodiment includes cap 27 for attaching to the cap 26 of handle portion 22. Although shown schematically, it is understood that each cap 26, 27 can include complementary structure for joining together, e.g. threads, snap features, or the like. Sheath 28 has a lumen 64 that extends through both the head portion 62 and tube portion 60, which is sized to accommodate closure device D. In particular, the inner diameter of lumen 64 is sized and configured to accommodate a domed or curved portion of closure D in a folded or curled (e.g. approximately half of its expanded or natural diameter) state.

Closure device D in a particular embodiment includes an anchoring member A, a stem S, and a suture or filament F. Such embodiments can also include a pad or buffer (e.g. of biological material such as small intestinal submucosa (SIS)), a locking member, and/or other parts (not shown). It is noted here that anchoring member A may be a flexible or shape-alterable curved piece designed to contact a tissue portion adjacent a hole to be closed, to partly or wholly cover the hole. In cases where it engages tissue around the entire hole, member A may be thought of as a seal. Stem S extends from a proximal (e.g. concave) portion of anchoring member A, and may include a series of protrusions to aid in locking device D. Stem S is flexible but semi-rigid in the illustrated embodiment. In other embodiments stem S may be left out, replaced by a thread, suture or other type of filament (e.g. part of or attached to filament F). Filament F is connected to stem S in this embodiment (e.g. threaded through a hole in a proximal part of stem S) and extends proximally from stem S. Buffer(s) and locking member(s) may be placed around and/or along stem S and/or filament F in an original condition and moved along them so the hole is covered by and/or opposite anchoring member A, and anchoring member A being held in place by stem S (and any locking member(s) or buffer(s).

As noted previously, a winding mechanism can be provided in particular embodiments. In one example, winding mechanism 30 includes a body 70 and a distally-extending tube portion 72. On the side of body 70 in the illustrated embodiment is a knob 74 attached to an axle 76 that extends through body 70. Axle 76 has an opening 78 (e.g. a radial hole or slot) in this embodiment through which a portion of a suture or filament attached to or a part of closure D is threaded. In particular embodiments, the filament is fixed to axle 76 or prevented from being withdrawn through hole 78, as by a knot in the filament or by known joining methods. Tube portion 72 is long, being adapted to extend through handle 22, sleeve 24 and at least part of sheath 28, and includes a lumen 80 through which the filament attached to or winding around axle 76 passes.

In the assembled condition of this embodiment of system 20, its parts are inserted through each other in a generally nested fashion. Sleeve 24 is around the outside of tube portion 60 of sheath 28, so that sheath 28 and tube portion 50 of sleeve 24 can slide with respect to each other. Handle 22 may be initially linked to sheath 28 by connecting or holding caps 26, 27 to each other (as by snapping or threading together), so that pulling or pushing handle 22 moves sheath 28, and if sleeve 24 is being held, pulling or pushing handle 22 moves sheath 28 through sleeve 24. Tube portion 72 of winding mechanism 30 is inserted through lumen 48 of handle 22, and tube portion 72 extends into tube portion 60 of sheath 28. Device D is loaded into sheath 28 so that parts (e.g. at least anchoring member A, stem S) are within sheath 28, or anchoring member A is outside of and preferably against the end of sheath 28. Filament F of device D extends through sheath 28 and into and through lumen 80 of winding mechanism 30, attaching to axle 76. In the initial condition, system 20 is configured with sleeve 24 at or adjacent the distal end of sheath 28, so that sleeve 24 engages the hemostatic valve essentially first when system 20 is used.

An example of the use of above-described embodiment of system 20 is described below in the context of closing a septal defect. It will be understood that such embodiments may be used in other contexts, for closing cutaneous or internal holes (e.g. fistulae or vascular or other openings made during treatment or diagnosis) in a patient.

Figure 6:
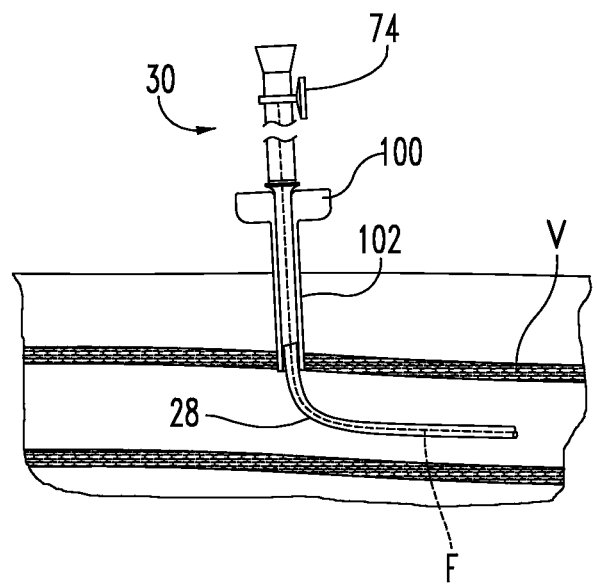
FIGS. 6-8 are schematic views of an application of the embodiment shown in FIG. 1.
Figure 7:
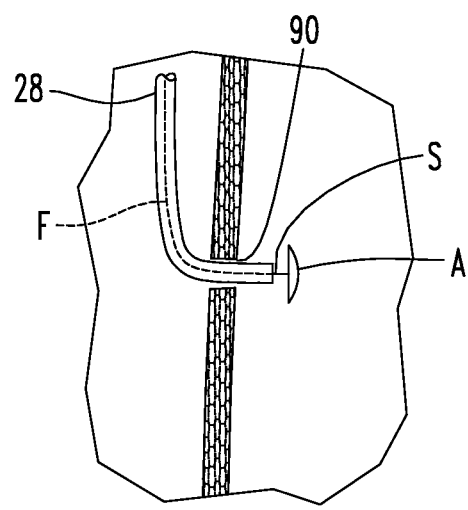
Figure 8:
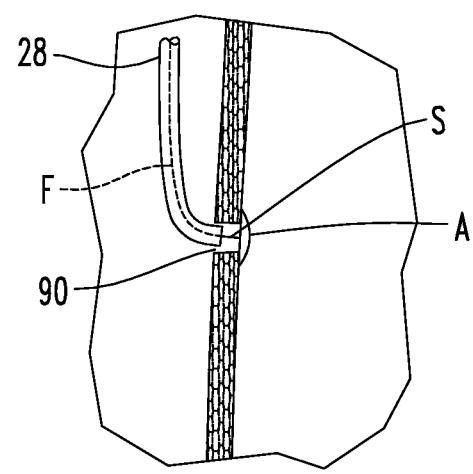

To access a septal defect 90, an opening through skin tissue T and into a blood vessel V is made, which opening may be occupied by a hemostatic valve 100 with a cannula 102 (e.g. FIG. 6-8). System 20 is inserted into vessel V and maneuvered through vessel V and perhaps other vessels of the circulatory system to the heart, and through the septal defect. In particular examples, system 20 may be passed through a catheter previously placed through the septal defect, or may be moved along or beside a guide wire so placed. In cases employing valve 100, as flange 52 or other part of sleeve 24 engages valve 100, and prevents further insertion of sleeve 24, sheath 28 can continue to move through sleeve 24 and into the circulatory system. Alternatively, in some cases a portion of sleeve 24 will enter valve 100, and sleeve 24 will slide along sheath 28 until the head portion 62 of sheath 28 (or cap 27) contacts flange 52, pushing sleeve 24 through the valve until flange 52 contacts valve 100. Throughout this insertion, hemostasis is maintained by the cannula protruding into the vessel and its associated valve.

With sheath 28 extending through the defect, anchoring member A is moved beyond sheath 28 (if not already beyond sheath 28). One method of moving anchoring member A is by pushing it, as by using tube 72 of winding mechanism 30. As anchoring member A exits sheath 28, anchoring member A expands (e.g. unfolds) to a size having at least one dimension larger than sheath 28 and larger than the defect or other hole to be covered or closed. In embodiments having winding mechanism 30 or another structure including a tube 72 through handle 22, lock 46 may be engaged against tube 72 to hold tube 72 and handle 22 together. The user pulls back with handle 22, which pulls filament F and stem S through the defect and generally toward valve 100, and pulls anchoring member A back toward the septum in this example. Anchoring member A is engaged or pulled against the septum. Handle 22 may be uncoupled from sheath 28 (as by uncoupling caps 26, 27 of each part from each other) prior to pulling handle 22 back. By continuing to pull on handle 22 and thereby tensioning filament F, anchoring member A is forced against tissue and may thereby be expanded or assisted to expand to its fullest width and/or press firmly against the septum along a larger portion or area along the septum. In this way, the user can have confidence that anchoring member A has assumed its natural width and is across the hole in the vessel wall. In other embodiments, pulling handle 22 also pulls sheath 28 through sleeve 24, and moves winding mechanism 30 away from the patient.

When anchoring member A abuts or engages the septum, the user feels tautness or tension transmitted by filament F, and he or she can maintain that tension to ensure that anchoring member A is against the introducer valve. Once anchoring member A contacts the septum surface of the vessel, it is locked into place so that anchoring member A and/or parts noted above (e.g. a lock or a buffer material) close or cover the hole.

In embodiments having winding mechanism 30, with device D locked into place to seal or block the septal defect, the user turns knob 74 of winding mechanism 30. Turning knob 74 in this embodiment winds filament F around axle 76, increasing tension on filament F. Knob 74 is turned until the tension on filament F is released, as when the connection between filament F and stem S is severed. For example, knob 30 may be turned until filament F and/or a portion of stem S holding or adjacent filament F breaks. System 20 can then be withdrawn from the heart, through the vasculature and valve 100. In cases where the filament F adjacent stem S or a portion of stem S adjacent filament F breaks, since filament F remains connected to winding mechanism 30, withdrawing system 20 also withdraws filament F fully from the patient. A separate closure for the hole made in vessel V for passing system 20 to the heard can be inserted through valve 100, if the physician deems it necessary.

While the disclosure has been illustrated and described in detail in the drawings and foregoing description, the same is to be considered as illustrative and not restrictive in character, it being understood that only the most preferred embodiments have been shown and described, and that all changes and modifications that come within the spirit of the disclosure are desired to be protected. Features or aspects discussed in connection or in the context of one embodiment or part may be used with or incorporated into other embodiments, parts or aspects of this disclosure. In addition, all publications cited herein are indicative of the abilities of those of ordinary skill in the art and are hereby incorporated by reference in their entirety as if individually incorporated by reference and fully set forth.

What is claimed is:

1. An apparatus for inserting a device into a patient to close a tissue opening in the patient, comprising:
a handle portion having a gripping portion with an external surface for gripping by a user, a lumen extending through the gripping portion, and a cap at a distal end portion of the handle portion;
a sleeve having a proximal end and a flange at the proximal end, the sleeve defining a lumen; and
a sheath portion having a proximal end portion and an elongated tubular member extending from the proximal end portion, a lumen extending through the proximal end portion and the elongated tubular member, and a cap at a proximal end portion of the sheath portion for connecting to the cap of the handle portion for selective connection and separation of the sheath portion and handle portion;

wherein the flange of the sleeve is separated from the handle portion by the cap of the sheath portion, and the elongated tubular member of the sheath portion extends at least partially through the lumen of the sleeve, and wherein the sleeve and tubular member of the sheath portion are slidable with respect to each other along each other;

a closure device having an internal member for sealing or anchoring and a filament connected to the internal member, the internal member being initially within the sheath portion and the filament initially extending through at least a portion of the lumen of the sheath portion and the lumen of the handle portion; and a winding mechanism connected to the handle portion, the winding mechanism having a knob operatively connected to the filament so that when the knob is turned in a predetermined direction, tension is applied to the filament.

2. The apparatus of claim 1, wherein the winding mechanism includes an axle to which the filament is connected, wherein turning the knob turns the axle and winds the filament.

3. The apparatus of claim 1, wherein the handle portion includes a lock for selectively engaging a portion of the winding mechanism.

4. The apparatus of claim 3, wherein the lock includes an enlarged grip external of the handle portion and a projection extending from the enlarged grip through an outer surface of the handle portion and into the lumen of the handle portion, the lock having an engaged configuration in which the projection has a tight fit with a portion of the winding mechanism.

5. The apparatus of claim 1, wherein the sleeve is configured for insertion through a hemostatic valve, and the flange of the sleeve is configured to engage the hemostatic valve, so that the flange cannot move entirely through the valve.

6. The apparatus of claim 1, further comprising a hemostatic valve for percutaneous insertion in a blood vessel, and wherein at least a portion of the sleeve extends through the valve to allow at least a portion of the sheath and the internal member into the vessel.

7. The apparatus of claim 1, wherein the handle portion does not extend into the sleeve.

8. The apparatus of claim 1, wherein the knob is connected to an axle to which the filament is connected, and the knob and axle are adapted to apply sufficient tension on the filament by turning the knob to break the filament.

9. An apparatus for inserting a device into a patient to close a tissue opening in the patient, comprising:

a handle portion having a gripping portion with an external surface for gripping by a user, a lumen extending through the gripping portion;

a sleeve having a proximal end and a flange at the proximal end, the sleeve defining a lumen; and a sheath portion having a proximal end portion and an elongated tubular member extending from the proximal end portion, a lumen extending through the proximal end portion and the elongated tubular member, wherein the elongated tubular member of the sheath portion extends at least partially through the lumen of the sleeve, and wherein the sleeve and tubular member of the sheath portion are slidable with respect to each other along each other;

a winding mechanism including a body, a knob external to the body fixed to an axle extending into the body, and a distally-extending tube portion, wherein the tube portion of the winding mechanism extends through the lumen of the handle portion; and a closure device having an internal member for sealing or anchoring and a filament connected to the internal member, the filament initially connected to the axle through the tube portion of the winding mechanism and lumen of the handle portion.

10. The apparatus of claim 9, wherein the handle portion has a distal end with a cap, and wherein the sheath portion has a proximal end with a cap adapted to connect to the cap of the handle portion for selective connection and separation of the sheath portion and handle portion.

11. The apparatus of claim 9, wherein the handle portion includes a lock extending through a side surface of the handle portion and into the lumen of the handle portion, adapted to selectively engage a portion of the winding mechanism.

12. The apparatus of claim 11, wherein the lock includes an enlarged grip external of the handle portion and a projection extending from the enlarged grip through an outer surface of the handle portion and into the lumen of the handle portion, the lock having an engaged configuration in which the projection has a tight fit with a portion of the winding mechanism.

13. The apparatus of claim 9, further comprising a hemostatic valve for percutaneous insertion in a blood vessel, and wherein at least a portion of the sleeve extends through the valve to allow at least a portion of the sheath and the internal member into the vessel.

14. The apparatus of claim 9, wherein the handle does not extend into the sleeve.

* * * * *